(12) United States Patent
Sutovsky et al.

(10) Patent No.: US 8,771,934 B2
(45) Date of Patent: Jul. 8, 2014

(54) INORGANIC PYROPHOSPHATE AND USES THEREOF

(71) Applicant: The Curators of the University of Missouri, Columbia, MO (US)

(72) Inventors: Peter Sutovsky, Columbia, MO (US); Young-Joo Yi, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 13/708,728

(22) Filed: Dec. 7, 2012

(65) Prior Publication Data

US 2013/0164732 A1 Jun. 27, 2013

Related U.S. Application Data

(60) Provisional application No. 61/630,345, filed on Dec. 9, 2011.

(51) Int. Cl.
*A01N 1/02* (2006.01)
(52) U.S. Cl.
USPC .............................................................. 435/2
(58) Field of Classification Search
None
See application file for complete search history.

(56) References Cited

U.S. PATENT DOCUMENTS

| 4,329,337 | A | 5/1982 | Sexton |
| 5,958,907 | A * | 9/1999 | Welsh ........................... 514/108 |
| 6,309,815 | B1 | 10/2001 | Tash et al. |
| 2002/0115055 | A1 | 8/2002 | Matta |

FOREIGN PATENT DOCUMENTS

| WO | WO 8302952 A1 * | 9/1983 |
| WO | WO 2006/130884 A2 | 12/2006 |

OTHER PUBLICATIONS

Lindemann, Ch.B., and Rikmenspoel, R. "Sperm flagellar motion maintained by ADP", Experimental Cell Research 1972, vol. 73, pp. 255-259.*
Terkeltaub, R.A. "Inorganic pyrophosphate generation and disposition in pathophysiology", American Journal of Physiology. Cell Physiology 2001, vol. 281, pp. C1-C11.*
Abeydeera et al., "Maturation in vitro of pig oocytes in protein-free culture media: fertilization and subsequent embryo development in vitro," *Biol Reprod* 58:1316-1320, 1998.
Baykov et al., "Cytoplasmic inorganic pyrophosphatase," *Prog Mol Subcell Biol* 23:127-150, 1999.
Chen et al., "Pyrophosphatase is essential for growth of *Escherichia coli*," *J Bacteriol* 172:5686-5689, 1990.
Chi et al., "The primordial high energy compound: ATP or inorganic phosphate," *J Biol Chem* 275:35677-35679, 2000.
Davidson et al., "Inorganic pyrophosphate is located primarily in the mitochondria of the hepatocyte and increases in parallel with the decrease in light-scattering induced by gluconeogenic hormones, butyrate and ionophore A23187," *Biochem J* 254:379-384, 1988.
Da Silva et al., "Protein phosphorylation by inorganic pyrophosphate in yeast mitochondria," *Biochem Biophys Res Commun* 178:1359-1364, 1991.
Fleisch et al., "Effect of pyrophosphate on hydroxyapatite and its implications in calcium homeostasis," *Nature* 212:901-903,1966.
Fleisch et al., "Isolation from urine of pyrophosphate, a calcification inhibitor," *Am J Physiol* 203:671-675, 1962.
Hoelzle et al., "Inorganic pyrophosphatase in uncultivable hemotrophic mycoplasmas: identification and properties of the enzyme from *Mycoplasma suis*," *BMC Microbiol*, 10:194, 2010.
Islam et al., "Pyrophosphatase of the roundworm *Ascaris suum* plays an essential role in the worm's molting and development," *Infect Immun* 73(4):1995-2004, 2005.
Johnson et al., "Artificial insemination of swine: Fecundity of boar semen stored in Beltsville TS (BTS), Modified Modena (MM), or MR-A and inseminated on one, three and four days after collection," *Zuchthygiene* 23:49-55, 1988.
Johnson et al., "Differential mechanisms of inorganic pyrophosphate production by plasma cell membrane glycoprotein-1 and B10 in chondrocytes," *Arthritis Rheum* 42(9):1986-1997, 1999.
Johnson et al., "Mitochondrial oxidative phosphorylation is a downstream regulator of nitric oxide effects on chondrocyte matrix synthesis and mineralization," *Arthritis Rheum* 43(7):1560-1570, 2000.
Johnson et al., "Storage of boar semen," *Anim Reprod Sci* 62:143-172, 2000.
Lahti, "Microbial inorganic pyrophosphatases," *Microbiol Rev* 47(2):169-178, 1983.
Lundin et al., "Yeast PPA2 gene encodes a mitochondrial inorganic pyrophosphatase that is essential for mitochondrial function," *J Biol Chem* 266:12168-12172,1991.
Lundin et al., "Characterization of a mitochondrial inorganic pyrophosphatase in *Saccharomyces cerevisiae*," *Biochim Biophys Acta* 1098:217-223, 1992.
Pate et al., "Resolution of the competitive inhibitory effects of lithium and AMPPNP on the beat frequency of ATP-reactivated, demembranated sea urchin sperm flagella," *J Muscle Res Cell Motil* 6(4):507-512, 1985.

(Continued)

*Primary Examiner* — Allison Ford
*Assistant Examiner* — Michelle F Paguio Frising
(74) *Attorney, Agent, or Firm* — Dentons US LLP

(57) ABSTRACT

The present invention provides a new and improved sperm stimulating additive comprising a certain amount of inorganic pyrophosphate (PPi). Addition of PPi in the media for human/animal in vitro fertilization (IVF) improves fertilization rate; addition of PPi in the semen extender for farm animal artificial insemination (AI) may improve pregnancy rates; furthermore, mammalian oocytes matured in vitro in a medium including PPi attain improved fertilization and developmental potential, while embryos cultured in medium supplemented with PPi have improved development to blastocyst.

12 Claims, 8 Drawing Sheets

(56) References Cited

OTHER PUBLICATIONS

Peller et al., "On the free-energy changes in the synthesis and degradation of nucleic acids," *Biochemistry* 15:141-146, 1976.

Pereira-Da-Silva et al., "Inorganic pyrophosphate gives a membrane potential in yeast mitochondria, as measured with the permeant cation tetraphenylphosphonium," *Arch Biochem Biophys* 304:310-313, 1993.

Pursel et al., "Freezing of boar spermatozoa: fertilizing capacity with concentrated semen and a new thawing procedure," *J Anim Sci* 40:99-102, 1975.

Rodriguez-Miranda et al., "Extracellular adenosine 5'-triphosphate alters motility and improves the fertilizing capability of mouse sperm," *Biol Reprod* 79(1):164-171, 2008.

Rosen et al., "Differential effects of aging on human chondrocyte responses to transforming growth factor beta: increased pyrophosphate production and decreased cell proliferation," *Arthritis Rheum* 40:1275-1281, 1997.

Rosenthal et al., "Retinoic acid stimulates pyrophosphate elaboration by cartilage and chondrocytes," *Calcif Tissue Int* 59:128-133, 1996.

Rosenthal et al., "Thyroid hormones induce features of the hypertrophic phenotype and stimulate correlates of CPPD crystal formation in articular chondrocytes," *J Rheumatol* 26:395-401, 1999.

Russell et al., "Inorganic pyrophosphate in plasma in normal persons and in patients with hypophosphatasia, osteogenesis imperfecta and other disorders of bone," *J Clin Invest* 50:961-969, 1971.

Ryan et al., "Transduction mechanisms of porcine chondrocyte inorganic pyrophosphate elaboration," *Arthritis Rheum* 42(3):555-560, 1999.

Sivula et al., "Evolutionary aspects of inorganic pyrophosphatase," *FEBS Lett* 454:75-80, 1999.

Sonnewald, "Expression of *E. coli* inorganic pyrophosphatase in transgenic plants alters photoassimilate partitioning," *Plant J* 2:571-581, 1992.

Terkeltaub et al, "Inorganic pyrophosphate generation and disposition in pathophysiology," *Am J Physiol Cell Physiol* 281:C1-C11, 2001.

Yeste et al., "Boar spermatozoa and prostaglandin F2α. Quality of boar sperm after the addition of prostaglandin F2α to the short-term extender over cooling time," *Anim Reprod Sci* 108:180-195, 2008.

Yoo et al., "Efficient production of cloned bovine embryos using cdc2 kinase inhibitor," abstract, *Reprod Domest Anim* 38(6):444-450, 2003.

\* cited by examiner

INORGANIC PYROPHOSPHATE AND USES THEREOF

STATEMENT REGARDING FEDERALLY SPONSORED RESEARCH

This invention was made with Government support under Grant Nos. 2007-35203-18274 and 2011-67015-20025 from the USDA National Institute of Food and Agriculture (USDA-NIFA). The Government has certain rights in the invention.

CROSS REFERENCE TO RELATED APPLICATIONS

This application claims the priority of U.S. Provisional Appl. Ser. No. 61/630,345, filed Dec. 9, 2011, the entire disclosure of which is incorporated herein by reference.

FIELD OF THE INVENTION

The present invention relates to a composition and method of use for artificial insemination. More specifically, the invention relates to a sperm-stimulating additive to be employed in artificial insemination of farm animals and in vitro fertilization and embryo culture in human infertility clinics.

BACKGROUND OF THE INVENTION

Artificial insemination (AI) is a common technique in swine and cattle farming. Freshly ejaculated boar semen must be stored in extender solution for preservation at 15-18° C. or 4-5° C., and bull semen has to be extended prior to cryopreservation and storage in liquid nitrogen. Various types of extender solutions and compounds have been developed to reduce the metabolic activity of sperm and allow for extended preservation. However, new and improved culture media and/or sperm extenders are needed to improve artificial insemination in animals and in vitro fertilization and embryo culture in humans.

SUMMARY OF THE INVENTION

In one aspect, the invention provides a sperm preservation media comprising inorganic pyrophosphate (PPi). In one embodiment, the concentration of PPi is between about 1 μM and about 200 μM. In another embodiment, concentration of PPi is between about 1 μM and about 20 μM. In another embodiment, the concentration of PPi is about 10 μM. In still another embodiment, the preservation media is used to preserve sperm from a porcine.

In another aspect, the invention provides a media for sperm transfer comprising inorganic pyrophosphate (PPi). In one embodiment, the concentration of PPi is between about 1 μM and about 200 μM. In another embodiment, the concentration of PPi is between about 1 μM and about 20 μM.

Another aspect of the invention provides a media for in vitro fertilization (IVF) or artificial insemination (AI) comprising inorganic pyrophosphate (PPi). In one embodiment, the concentration of PPi is between about 1 μM and about 200 μM. In another embodiment, the concentration of PPi is between about 1 μM and about 20 μM.

In another aspect, the invention provides a semen sexing method, comprising: (a) seperating a mixed sperm suspension in a first culture medium into a population of x-bearing or y-bearing sperm with the aid of an elutant medium; (b) preserving the x-bearing or y-bearing sperm in a second culture medium, wherein, inorganic pyrophosphate (PPi) is added to the first culture medium, the elutant medium or the second culture medium.

In still another aspect, the invention provides a method of sperm preservation comprising storing sperm in a media comprising inorganic pyrophosphate (PPi). In one embodiment, the concentration of PPi is between about 1 μM to about 200 μM. In other embodiments, the concentration of PPi is between about 1 μM to about 20 μM or the concentration of PPi is about 10 μM. In still another embodiment, the sperm is stored in the media comprising PPi for up to 10 days.

Another aspect of the invention provides a method of in vitro fertilization (IVF) comprising contacting an oocyte with sperm in the presence of inorganic pyrophosphate (PPi). In one embodiment, the concentration of PPi is between about 1 μM to about 200 μM. In another embodiment, the concentration of PPi is between about 1 μM to about 20 μM. In another embodiment, the sperm is stored in the presence of PPi.

In another aspect, the invention provides a method of culturing an embryo comprising culturing an embryo in a media comprising inorganic pyrophosphate.

In still another aspect, the invention provides a method of artificial insemination comprising providing sperm and inorganic pyrophosphate (PPi) to the reproductive tract of a female. In an embodiment, the PPi is gradually released into the reproductive tract of the female.

Another aspect of the invention provides a method of maturing an oocyte in vitro comprising culturing the oocyte in a media comprising inorganic pyrophosphate.

DETAILED DESCRIPTION OF THE INVENTION

Figure 1:
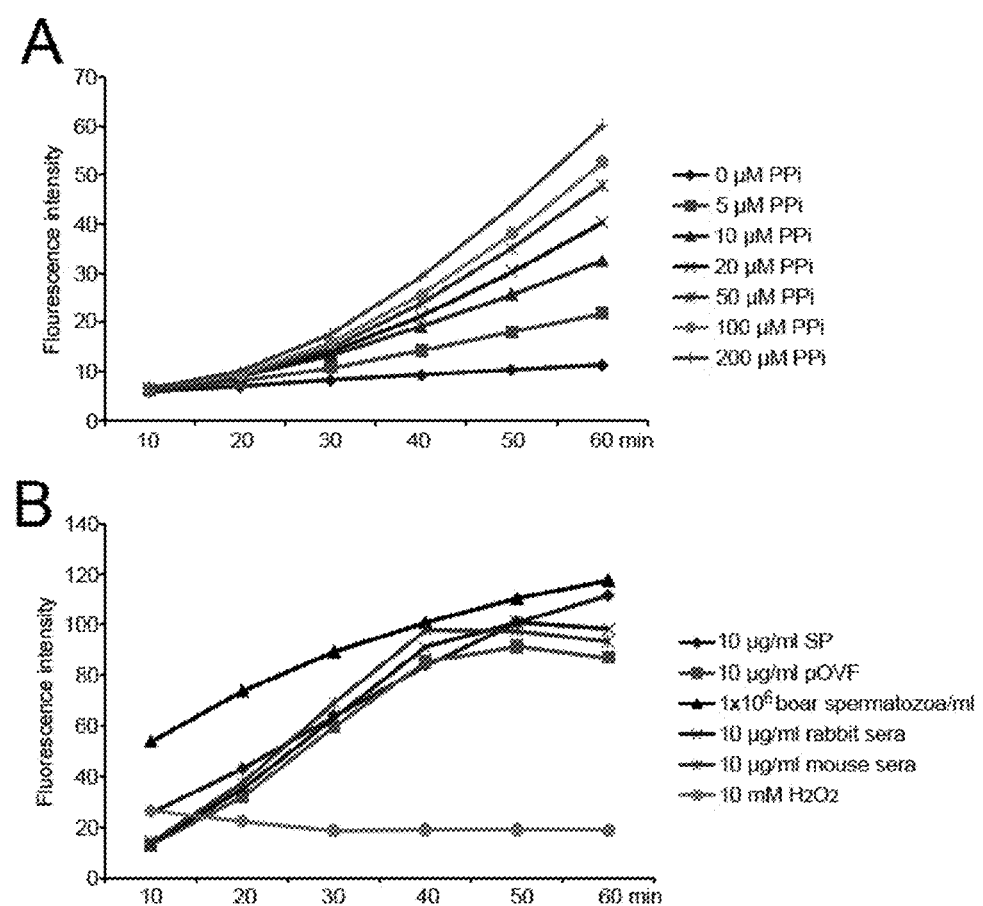
FIG. 1: Shows measurement of pyrophosphate (PPi) content by fluorometric assay. (A) Fluorescence intensity of PPi standards (final conc. 0-200 μM PPi). (B) PPi assay with boar seminal plasma (SP), porcine oviductal fluids (pOVF), rabbit sera, mouse sera (final conc. 10 μg/ml), boar spermatozoa ($1 \times 10^6$ spermatozoa/ml) and 10 mM $H_2O_2$ working solution (negative control). The fluorescence intensities were measured at multiple time points to follow the reaction kinetics (Excitation 530 nm; emission 590 nm). Experiments were repeated three times. Values are expressed as the mean of fluorescence intensity.

The present invention provides novel media and methods for sperm preservation, embryo culture, in vitro fertilization (IVF), artificial insemination (AI). In particular, the present invention represents an advance in the art in that it reports and confirms that inorganic pyrophosphate (PPi) exists in spermatozoa, seminal plasma (SP) and oviductal fluids (OVF) of mammalian species, though the previous studies have shown that the concentration of cytosolic PPi is precisely regulated in mammalian cells (Baykov et al., *Prog Mol Subcell Biol* 23:127-150, 1999; Sivula et al., *FEBS Lett* 454:75-80, 1999). In one aspect of the invention, PPi might therefore be used as an energy source for sperm viability.

In one embodiment, the present invention provides a new and improved sperm preservation media, also referred to as sperm extender that can extend semen storage period and maintain sperm viability, and thus improve AI in animals. The invention also provides a new and improved culture media for embryo transfer in animals.

In another embodiment, invention provides a new and improved method of IVF and AI as well as embryo culture media in an animal and human clinic.

In still another aspect of the invention, a new and improved method for semen sexing employing PPi is described. The present semen sexing method comprises the step of adding a certain amount of PPi in the media during a semen sexing procedure to enhance the sperm longevity and viability. For instance, according to certain embodiments of the invention, the present semen sexing method may comprise the step of adding PPi in the starting sperm processing media (with both x- and y-bearing sperm; before the conventional separation/sorting step), in the eluting media, or in the sex-separated sperm media.

Traditionally, Beltsville thawing solution (BTS) is added to frozen-thawed sperm as a thawing solution, and is also used for liquid storage for 3-5 days (Johnson et al., *Zuchthygiene* 23:49-55, 1988). Liquid semen extended by BTS has typically been utilized for AI due to its simple composition and developments of transportation. However, the motility of sperm preserved in extender gradually decreases during storage from natural aging, loss of ATP and cAMP, as well as reduced calcium uptake (Johnson et al., *Anim Reprod Sci* 62 143-172, 2000). Extended semen preserved for 5 days after collection shows a reduction in farrowing rates of approximately 50% compared to semen preserved for 2 days after collection, which shows a reduction in farrowing rates of approximately 65-70% (Johnson et al., *Anim Reprod Sci* 62 143-172; Johnson et al., *Zuchthygiene* 23:49-55, 1988; Johnson and Rath, (Eds), *Proc. 2nd Int. Conf. Deep Freezing Boar Semen. Reprod. Domest. Anim., Suppl.* 1, p. 402, 1991; Rath et al., (Eds) *Proc. Int. Conf. Deep Freezing of Boar Semen. Reprod. Domest. Anim. Suppl.* 1. p. 342, 1996; Johnson, *Proc. 15th Int. Pig Vet. Sci. Congress* 1, 225-229, 1998). Recently, Yeste et al. (*Anim Reprod Sci* 108:180-195, 2008) suggested that addition of prostaglandin $F_{2\alpha}$ ($PGF_{2\alpha}$) to sperm diluted in BTS maintained better sperm viability and motility after 6 days of cooling.

Inorganic pyrophosphate (PPi) is a potent, mineral-binding small molecule inhibitor of crystal nucleation and growth (Fleisch et al., *Nature* 212:901-903, 1966), and presents in the extracellular matrix of most tissues and body fluids including plasma (Fleisch et al., *Am J Physiol* 203:671-675, 1962; Russell et al., *J Clin Invest* 50:961-969, 1971). PPi metabolism has been observed in cultured hepatocytes and chondrocytes (Davidson et al., *Biochem J* 254:379-384, 1988; Johnson et al., 1999; Rosen et al., *Arthritis Rheum* 40:1275-1281, 1997; Rosenthal et al., *Calcif Tissue Int* 59:128-133, 1996; Rosenthal et al., *J Rheumatol* 26:395-401, 1999; Ryan et al., *Arthritis Rheum* 42:555-560, 1999). The intracellular PPi is generated in the mitochondria, and intra- and extracellular PPi concentrations are regulated by mitochondrial energy metabolism (Davidson et al., *Biochem J* 254:379-384, 1988; Johnson et al., *Arthritis Rheum* 43:1560-1570, 2000). In prokaryotes, PPi provides "high energy" compound, and is able to substitute for ATP in glycolysis-related reactions under attenuated respiration (Chi et al., *J Biol Chem* 275: 35677-35679, 2000). Moreover, PPi produces a mitochondrial membrane potential with PPA (Pereira-da-Silva et al., *Arch Biochem Biophys* 304:310-313, 1993), and ATP-derived PPi serves as a phosphate donor in protein phosphorylation in yeast mitochondria as well as in mammalian cells (da Silva et al., *Biochem Biophys Res Commun* 178:1359-1364, 1991; Terkeltaub et al, *Am J Physiol Cell Physiol* 281:C1-C11, 2001). Consequently, PPi may be used as an energy source for viability.

Cellular PPi is yielded by various biosynthetic processes, and hydrolyzed to two inorganic phosphates (Pi) by inorganic pyrophosphatase (PPA1). PPA1 is a ubiquitous metal-dependent enzyme providing a thermodynamic pull for many biosynthetic reactions, such as DNA, RNA, protein, polysaccharide synthesis and cell life (Chen et al. 1990, Lundin et al. 1991, Sonnewald 1992, Lahti 1983, Peller 1976). The PPA1 has been detected in bacteria (Chen et al. 1990) and yeast (Lundin et al. 1991), and the soluble PPA1 was identified and characterized in *Mycoplasma suis*, which belongs to hemotrophic bacteria that attach to the surface of host erythrocytes (Hoelzle et al.). However, the PPi has not been used in any media related to sperm preservation or AI or IVF procedures.

Figure 2:
FIG. 2: Shows generation of PPi. PPi is produced by the hydrolysis of ATP into AMP in cells. Inorganic pyrophosphatase (PPA1) catalyzes the hydrolysis of PPi to form 2 orthophosphates (2Pi), resulting in energy release.

The present invention identifies the PPi pathway as an important component of mammalian sperm physiology. Referring to FIG. 2, PPi ($P_2O_7^{4-}$) is formed by the hydrolysis of ATP into AMP in cells, then, hydrolyzed by inorganic pyrophosphatase (PPA1) into two molecules of inorganic orthophosphate (Pi). PPA1, an important enzyme for energy metabolism (Chen et al., *J Bacteriol* 172:5686-5689, 1990; Lundin et al., *J Biol Chem* 266:12168-12172, 1991), has been implicated in the regulation of metabolism, growth and development in plants (Sonnewald, *Plant J* 2:571-581, 1992), and even in the development and molting in the parasitic roundworm *Ascaris* (Islam et al., *Infect Immun* 73:1995-2004, 2005). During cell division of *S. cerevisiae*, PPA1 is essential for mitochondria genome replication (Lundin et al., *Biochim Biophys Acta* 1098; 217-223, 1992).

While PPA1 is detectable in the sperm tail connecting piece, harboring sperm centriole and anchoring flagellar outer dense fibers and microtubule doublets, the invention suggests that from these locations, the PPi-metabolizing pathway may convey energy for flagellar movement and for acrosomal function during sperm-zona penetration. In addition, the invention also suggests that the PPi pathway in the sperm head and flagellum may support protein phosphorylation during sperm capacitation that is observed both in vitro and in vivo, in the oviductal sperm reservoir.

The invention further describes the ability of mammalian spermatozoa to utilize PPi as an energy source during sperm transport and sperm-egg interactions, as the spermatozoa undergo capacitation, acrosome reaction and sperm-zona penetration. It is presently disclosed that PPi can be used as a stable, inexpensive energy source to improve sperm viability during semen storage and transfer for large animal biotechnology and to enhance sperm penetration and fertilization rates enhance for assisted reproductive therapy in mammalian species (including humans). The invention further provides the addition of PPi in the culture media, the sperm extender, the IVF media, or in media employed in sperm sexing to provide beneficial effects in sperm preservation and fertilization, such as increasing sperm longevity and viability during sperm preservations and transfers and maintaining and enhancing sperm viability, penetration and fertilization rates during fertilization procedures.

Media of the present invention may therefore comprise PPi, the concentration of which may vary depending on the animal species. In certain embodiments, media of the present invention may comprise about 1 to 200 μM of PPi. In another embodiment, media of the present invention may comprise about 1 to 20 μM. The present invention may be employed for various mammals, including farm animals, such as, boar and bull.

For IVF or AI, PPi may be directly added or gradually released into the media. If needed, PPi release can be exactly controlled/modulated during AI, especially when the PPi-containing slow release gel is employed as a part of AI catheter, to gradually release PPi into the female reproductive tract.

Unless otherwise defined, all technical and scientific terms used herein have the same meaning as commonly understood by one of ordinary skill in the art to which this invention belongs. All publications, patent application, patents, and other references mentioned herein are incorporated by reference in their entirety.

EXAMPLES

The following disclosed embodiments are merely representative of the invention which may be embodied in various forms. Thus, specific structural, functional, and procedural details disclosed in the following examples are not to be interpreted as limiting.

Example 1

Semen Collection and Processing

Semen was collected from proven fertile adult Duroc boars 15-22 months of age under the guidance of approved Animal Care and Use Committee (ACUC) protocols of the University of Missouri-Columbia (UM-C). The boars were placed on a routine collection schedule of one collection per week. The sperm-rich fraction of ejaculate was collected into an insulated vacuum bottle. Sperm-rich fractions of ejaculates with greater than 85% motile spermatozoa were used. Semen volumes were determined with a graduated cylinder. Sperm concentrations were estimated by a hemocytometer (Fisher Scientific, Houston, Tex.). The percentage of motile spermatozoa was estimated at 38.5° C. by light microscopy at 250× magnification. Semen was slowly cooled to room temperature (20-23° C.) by 2 h after collection and diluted with Beltsville thawing solution (BTS; 3.71 g glucose, 0.60 g trisodium citrate, 1.25 g ethylenediamine tetraacetic acid, 1.25 g sodium bicarbonate, 0.75 g potassium chloride, 0.06 g penicillin G, and 0.10 g streptomycin in 100.0 ml distilled water) (Pursel and Johnson 1975) diluent to a final concentration of $35 \times 10^6$ spermatozoa/ml in 100 ml of BTS diluent. The diluted semen was stored in Styrofoam™ boxes at room temperature for 10 days. Unless otherwise noted, all chemicals used in this study were purchased from Sigma Chemical Co. (St. Louis, Mo.).

Example 2

Collection and in Vitro Maturation (IVM) of Porcine Oocyte

Ovaries were collected from prepubertal gilts at a local slaughterhouse and transported to the laboratory in a warm box (25-30° C.). Cumulus oocyte complexes (COCs) were aspirated from antral follicles (3-6 mm in diameter), washed three times in HEPES-buffered Tyrode lactate (TL-HEPES-PVA) medium containing 0.01% (w/v) polyvinyl alcohol (PVA), and then washed three times with maturation medium (Abeydeera et al., *Biol Reprod* 58:1316-1320, 1998). Each time, a total of 50 COCs were transferred to a 4-well multidish (Nunc, Roskilde, Denmark) containing 500 µl of maturation medium that had been covered with mineral oil and equilibrated at 38.5° C. with 5% $CO_2$ in the air. The medium used for oocyte maturation was tissue culture medium (TCM) 199 (Gibco, Grand Island, N.Y.) supplemented with 0.1% PVA, 3.05 mM D-glucose, 0.91 mM sodium pyruvate, 0.57 mM cysteine, 0.5 µg/ml LH (L5269, Sigma), 0.5 µg/ml FSH (F2293, Sigma), 10 ng/ml epidermal growth factor (E4127, Sigma), 10% porcine follicular fluid, 75 µg/ml penicillin G, and 50 µg/ml streptomycin. After 22 h of culture, the oocytes were washed twice and cultured in TCM199 without LH and FSH for 22 h at 38.5° C., 5% $CO_2$.

Example 3

In Vitro Fertilization (IVF) and Culture of Porcine Oocyte

After oocyte maturation, cumulus cells were removed with 0.1% hyaluronidase in TL-HEPES-PVA medium and washed three times with TL-HEPES-PVA medium and Tris-buffered (mTBM) medium (Abeydeera et al., *Biol Reprod* 58:1316-1320, 1998) containing 0.2% BSA (A7888, Sigma), respectively. Thereafter, 25-30 oocytes were placed into each of four 50 µl drops of the mTBM medium, which had been covered with mineral oil in a 35 mm polystyrene culture dish. The dishes were allowed to equilibrate in the incubator for 30 min until spermatozoa were added for fertilization. One ml of liquid semen preserved in BTS diluent was washed twice in PBS containing 0.1% PVA (PBS-PVA) at 800×g for 5 min. At the end of the washing procedure, the spermatozoa were resuspended in mTBM medium. After appropriate dilution, 50 µl of this sperm suspension was added to 50 µl of the medium that contained oocytes to give a final sperm concentrations of $1-10 \times 10^5$ spermatozoa/ml. Different concentrations of inorganic pyrophosphate (PPi; S6422, Sigma) were added to fertilization drops (final concentrations; 0-20 µM) at the time of sperm addition. Oocytes were co-incubated with spermatozoa for 6 h at 38.5° C., 5% $CO_2$. At 6 h after IVF, oocytes were transferred into 100 µl NCSU23 containing 0.4% BSA (A6003, Sigma) for further culture during 16-20 h.

Example 4

Immunofluorescence and Evaluation of Fertilization Rates

Spermatozoa/oocytes were fixed in 2% formaldehyde for 40 min at room temperature, washed, permeabilized in PBS with 0.1% Triton-X-100 (PBS-TX), and blocked for 25 min in PBS-TX containing 5% normal goat serum. Spermatozoa/oocytes were incubated with rabbit polyclonal anti-pyrophosphatase 1 (PPA1) antibody (1:200 dilution; #ab96099, Abcam, San Francisco, Calif.) or rabbit polyclonal anti-ANKH antibody (1:200 dilution; #SAB1102581, Sigma) for 40 min, then incubated with goat-anti-rabbit (GAR)-IgG-TRITC (1/80 dilution; Zymed Inc., San Francisco, Calif.). For the evaluation of fertilization, oocytes/zygotes were fixed with 2% formaldehyde for 40 min at room temperature, washed three times with PBS, permeabilized with PBS-TX for 40 min at room temperature, and stained with 2.5 µg/ml DAPI (Molecular Probes, Eugene, Oreg.) for 40 min. Oocytes with two or more pronuclei and at least one sperm tail in the ooplasm were recorded as fertilized. In order to count the number of spermatozoa bound to zona pellucida or acrosome reacted spermatozoa, oocyte were fixed and stained with DAPI and acrosome-binding lectin PNA-FITC (Molecular Probes) after IVF 30 min ($5 \times 10^5$ spermatozoa/ml). Image acquisition was performed on a Nikon Eclipse 800 microscope (Nikon Instruments Inc., Melville, N.Y.) with Cool Snap camera (Roper Scientific, Tucson, Ariz.) and Meta-Morph software (Universal Imaging Corp., Downington, Pa.).

Figure 4:
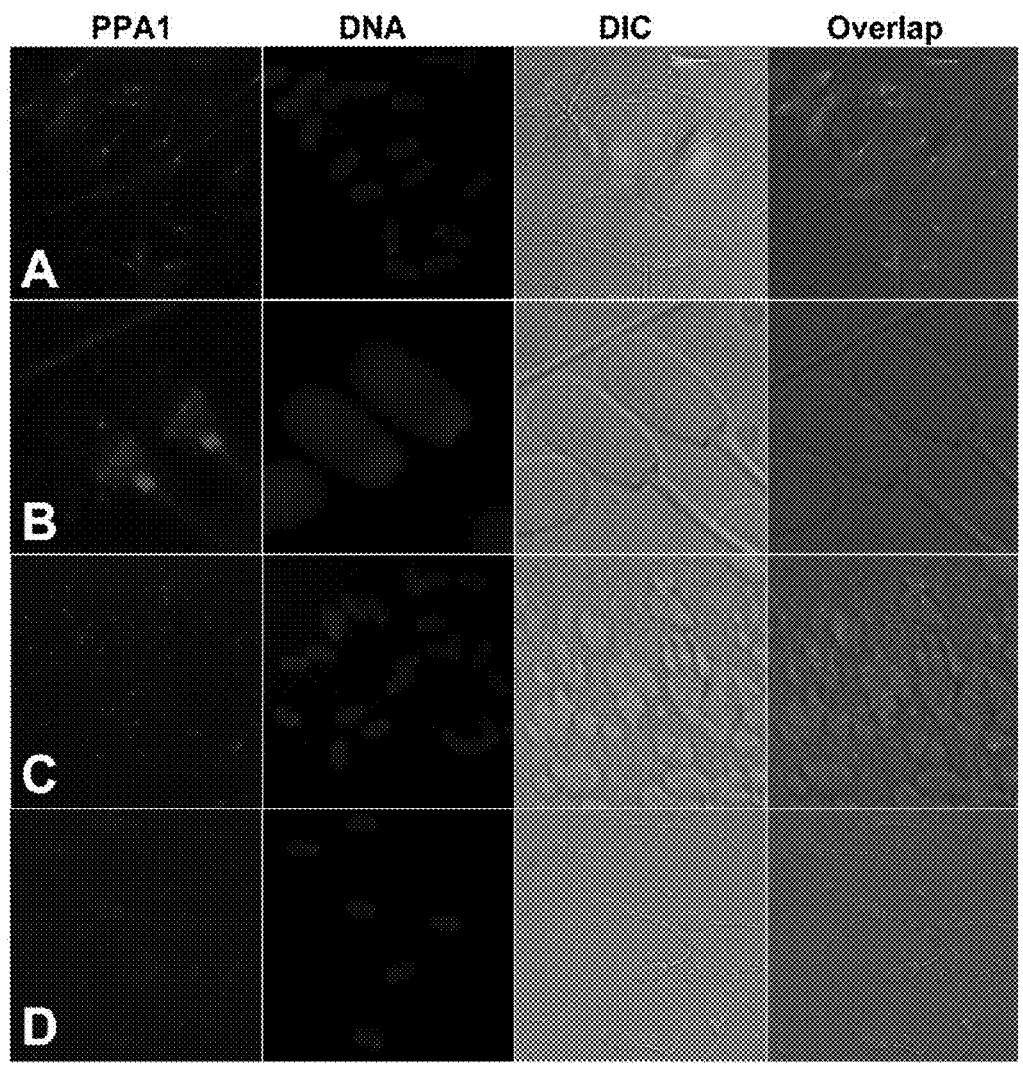
FIG. 4: Shows localization of inorganic pyrophosphatase (PPA1; red) in spermatozoa by immunofluorescence. (A, B) Whole-mount immunofluorescence of boar spermatozoa. Most prominent labeling is observed in the sperm tail connecting piece and in the postacrosomal sheath of the sperm head. (C) Identical labeling was observed in spermatozoa attached to oocyte zona pellucida at 30 min after gamete mixing during IVF. (D) Negative control with anti-PPA1 antibody immunosaturated with full-length PPA1 protein. DNA was counterstained with DAPI (blue). Epifluorescence micrographs were overlapped with parfocal transmitted light photographs acquired with DIC optics.

As shown in FIG. 4, immunofluorescence detected a prominent labeling of PPA1 in the sperm tail connecting piece and in the postacrosomal sheath of boar spermatozoa. Identical labeling was found in spermatozoa attached to oocyte zona pellucida at 30 min of in vitro fertilization, while negative control with anti-PPA1 antibody immunosaturated with full length recombinant PPA1 protein showed no such fluorescence, and neither did labeling of non-permeabilized spermatozoa.

Example 5

Western Blotting and Immunofluorescence

For western blotting, extracts of $1 \times 10^6$ spermatozoa/ml were loaded per lane. Spermatozoa were washed in PBS and boiled with loading buffer (50 mM Tris [pH 6.8], 150 mM NaCl, 2% SDS, 20% glycerol, 5% β-mercaptoethanol, 0.02% bromophenol blue). Gel electrophoresis was performed on 4-20% gradient gels (PAGEr® Precast gels, Lonza Rockland Inc., Rockland, Me.), followed by transfer to PVDF membranes (Millipore) using an Owl wet transfer system (Fisher Scientific) at a constant 50 V for 4 h. The membranes were sequentially incubated with 10% non-fat milk for 1 h, then with anti-PPA1 or anti-ANKH antibodies (1:2,000 dilution) overnight. The membranes were then incubated with an HRP-conjugated goat anti-rabbit IgG (GAR-IgG-HRP; 1:10,000 dilution) for 1 h. The membranes were reacted with chemiluminiscent substrate (SuperSignal, Pierce, Rockford, Ill.) and visualized by exposing to Kodak BioMax Light film (Kodak, Rochester, N.Y.).

Figure 3:
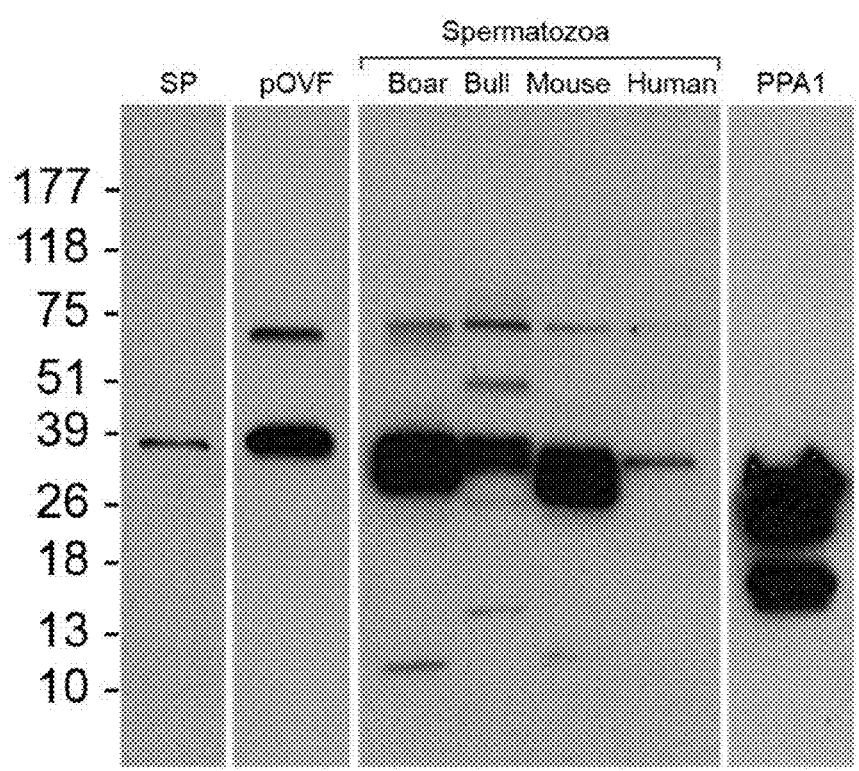
FIG. 3: Shows detection of inorganic pyrophosphatase (PPA1) by western blotting. Boar seminal plasma (SP; 20 μg/ml), porcine oviductal fluid (pOVF; 100 μg/ml), and boar, bull, mouse, and human spermatozoa (all at $1 \times 10^6$ spermatozoa/ml) were extracted to perform the protein analysis. Equal protein loads were used. Distinct band at ~32 kDa was detected by rabbit polyclonal anti-PPA1 antibody. The purified PPA1 (extreme right lane; 1 μg/ml; Sigma I1643) from *S. cerevisiae* was used as a control protein.

PPA1 was detected in mammalian seminal plasma, oviductal fluid and spermatozoa. As shown in FIG. 3, a protein band corresponding to the calculated mass of PPA1 (32 kDa) was detected in boar seminal plasma, in porcine oviductal fluid, and in boar, bull, mouse and human spermatozoa by Western blotting with rabbit polyclonal anti-PPA1 antibody. Minor bands of higher (~51 and 75 kDa) or lower mass (~13 kDa in boar and ~18 kDa in bull) were observed in each sperm sample, likely corresponding to posttranslational protein modification and degradation products of PPA1. The purified PPA1 from baker's yeast (*S. cerevisiae*), used as a positive control protein, also showed additional bands at 32 and 13 kDa.

Example 6

Pyrophosphate Assay

The measurement of pyrophosphate (PPi) was performed using PiPer™ Pyrophosphate Assay Kit (Cat. No. P22062, Molecular Probes), following manufacturer's protocol. The samples were prepared using 1× reaction buffer (Kit) with boar seminal plasma (SP), porcine oviductal fluids (OVF), rabbit sera, mouse sera (final conc. 10 μg/ml), boar spermatozoa ($1 \times 10^6$ spermatozoa/ml) and 10 mM $H_2O_2$ working solution (a negative control). The PPi standard was prepared by diluting the 50 mM PPi standard solution (final conc. 0-200 μM PPi). The working solution of 100 μM Amplex® Red reagent contains 0.02 U/ml inorganic pyrophosphatase (PPA1), 4 U/ml maltose phosphorylase, 0.4 mM maltose, 2 U/ml glucose oxidase and 0.4 U/ml HRP. In this reaction, PPA1 hydrolyzes PPi into two inorganic phosphates (Pi). In the presence of Pi, maltose phosphorylase converts maltose to glucose 1-phosphate and glucose. Glucose oxidase then converts glucose to gluconolactone and $H_2O_2$. In the presence of horseradish peroxidase (HRP), the $H_2O_2$ reacts with the Amplex® Red reagent (10-acetyl-3,7-dihyroxyphenoxazine) to generate resorufin, which is detected by fluorescence. Fifty μl samples were loaded into black 96-well (Coster-Corning, Corning, N.Y.), and then 50 μl working solutions were added into sample, respectively. The 96-well was incubated at 37.5° C. for 30 min, and fluorescence was measured at multiple time points to follow the kinetics of the reaction. Fluorescence intensity was measured by Thermo Fluoroskan Ascent (ThermoFisher Scientific) using 530 nm excitation and 590 nm emission wavelengths.

Results for measurement of the content of PPi in boar SP, pOVF and boar spermatozoa by a fluorometric assay are shown in FIGS. 1A and 1B. Different concentrations of PPi were measured as standards (0-200 μM PPi), and the fluorescence intensities increased progressively with increasing concentrations of PPi (FIG. 1A). The fluorescence intensities also increased in pOVF, SP, spermatozoa, mouse sera and rabbit sera. As shown in FIG. 1B, the boar spermatozoa, mouse sera, and rabbit sera showed higher fluorescence intensities than SP or pOVF at 40 min of acquisition (98.2-101.1 vs. 83.8 & 85.5). However, the intensities of pOVF, mouse sera and rabbit sera decreased gradually. Only the SP and spermatozoa showed continuous increase of fluorescence intensity during measurement (fluorescence intensities: 111.5 & 117.7 at 60 min, $p<0.05$). A negative control, 10 mM $H_2O_2$, showed a decreasing pattern, most likely due to bleaching of fluorescence.

Example 7

Flow Cytometric Analysis of Sperm Viability and Mitochondrial Membrane Potential Boar spermatozoa were washed twice with PBS-PVA, and sperm concentration was adjusted to $1 \times 10^6$ spermatozoa/ml in PBS-PVA. The sperm viability was assessed by LIVE/DEAD® Sperm Viability Kit (L-7011, Molecular Probes) which contains DNA dyes SYBR14 and propidium iodide (PI), following a manufacturer's protocol. Sperm samples (198 μl) were loaded onto a 96-well plate. SYBR14 (1 μl; final conc. 100 nM) and PI (1 μl; final conc. 12 μM) were added to sperm samples and incubated for 10 min at 37.5° C. in darkness. Flow cytometric analysis was performed using a Guava EasyCyte™ Plus flow cytometer (Guava Technologies, IMV Technologies, L'Aigle, France). For each sample, 5,000 events were analyzed by the Guava ExpressPro Assay program, using standard manufacturer settings. For assessment of sperm mitopotential, boar spermatozoa were stained with JC-1 (Cat. No. 4500-0250, MitoPotential Kit, IMV), and measured using manufacturer settings. For negative controls, DMSO or no staining solution was added to sperm samples.

Following an industry practice for boar semen storage, fresh boar semen was diluted in BTS extender and stored at room temperature (15-17° C.) for 10 days. The base extender is designed for short term storage (3-5 days); however, the storage period was prolonged up to 10 days to compare sperm viability and mitochondrial membrane potential between storage days 3 and 10 in the presence/absence of 10 μM PPi. As described above, sperm viability was assessed by flow cytometry using a SYBR14/PI viability kit and mitopotential was measured with JC-1 dye. Supplementation with PPi altered the histograms and scatter diagrams of fluorescence produced by the above probes a vehicle control, DMSO produced no fluorescence.

Figure 5:
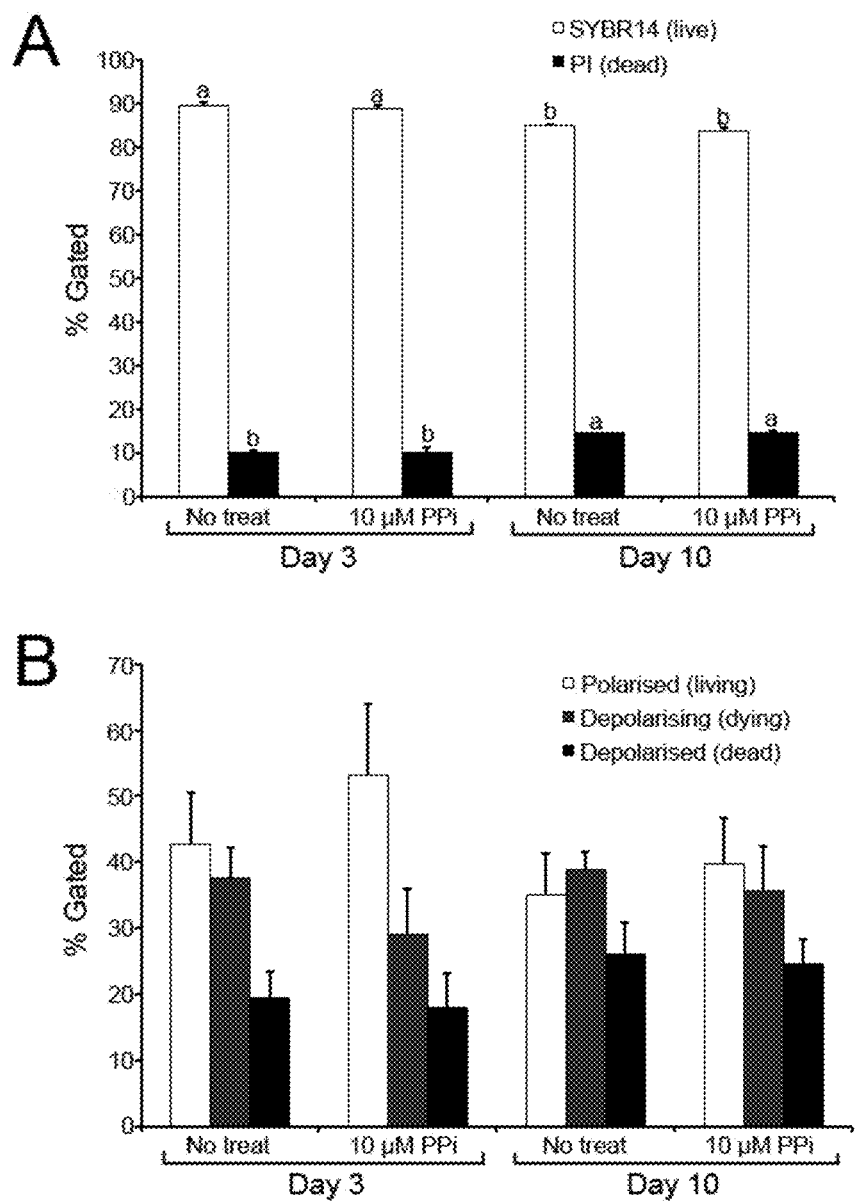
FIG. 5: Shows sperm viability and mitochondrial membrane potential during sperm storage with/without PPi. (A) Percentages of viable spermatozoa based SYBR14 (live sperm) and PI (dead sperm) labeling. (B) Percentages of spermatozoa with polarized (live), depolarizing (dying) and depolarized (dead) mitochondrial membranes. Experiments were repeated three times. Values are expressed as the mean percentages±SEM. Different superscripts a & b in each group of columns denote a significant difference at p<0.05.

FIGS. 5A and 5B compare the sperm viabilities and mitochondrial membrane potentials during sperm storage with and without PPi. As shown in FIG. 5A, the percentage of live spermatozoa was higher on day 3 than on day 10 ($p<0.05$), but there was no significant difference between control spermatozoa and those supplemented with 10 μM PPi. Contrary to viability, PPi supplementation augmented the content of metabolically active spermatozoa with polarized mitochondrial membranes on day 3 (FIG. 5B). Similar tendency was observed in spermatozoa preserved with 10 μM PPi for 10 days (FIG. 5B).

Example 8

Measurement of Proteasomal-Proteolytic Activity

The proteasomal-proteolytic and deubiquitinating activities, which are essential for fertilization, were assayed using specific fluorometric substrates Z-LLL-AMC, Z-LLVY-AMC, Z-LLE-AMC and ubiquitin-AMCs in spermatozoa stored for 3 and 10 days, with or without PPi. Alternatively, 10 μM PPi+BTS was added to semen preserved without PPi at the time of assay ("Add PPi" treatment). As a negative control, 10 μM MG132 (a proteasomal inhibitor) was added to sperm samples before assay.

Spermatozoa preserved in BTS with and without 10 μM PPi were loaded into a 96-well black plate (final sperm conc.

1×10⁶ spermatozoa/ml), and incubated at 37.5° C. with Z-LLE-AMC (a specific substrate for 20S chymotrypsin-like peptidyl-glutamylpeptide hydrolyzing [PGPH] activity not sensitive to MG132; final conc. 100 µM; Enzo Life Sciences, Plymouth, Pa.), Z-LLVY-AMC (a specific substrate for 20S proteasome and other chymotrypsin-like proteases, as well as calpains; final conc. 100 µM; Enzo), Z-LLL-AMC (a specific substrate for 20S chymotrypsin-like activity sensitive to proteasomal inhibitor MG132; final conc. 100 µM; BostonBiochem, Cambridge, Mass.) or ubiquitin-AMC (specific substrate for ubiquitin-C-terminal hydrolase activity; final conc. 1 µM; Enzo) for 1 h. Fluorogenic proteasomal core substrates are composed of a small peptide (LLL/LLE/LLVY) coupled to a fluorescent probe, aminomethylcoumarin (AMC). The intact AMC-coupled substrate does not emit fluorescence. In the presence of appropriate 20S core activity, the AMC molecule is cleaved off and becomes fluorescent. This emitted fluorescence was measured every 10 min for a period of 1 h, yielding a curve of relative fluorescence (no units). Fluorescence intensity was measured by Thermo Fluoroskan Ascent (Thermo Scientific), using a 380 nm excitation and 460 nm emission.

Figure 6A:
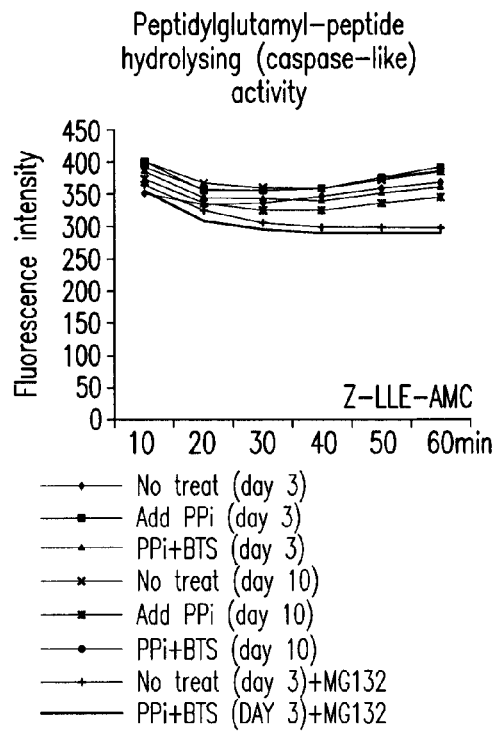
FIG. 6: Shows the effect of PPi on proteasomal enzymatic activities of stored boar spermatozoa. Fresh boar spermatozoa were stored in BTS with and without 10 μM PPi for 3 or 10 days (No treat/PPi+BTS). Proteasomal proteolytic and deubiquitinating activities were measured using specific fluorometric substrates Z-LLE-AMC (A), Z-LLVY-AMC (B), Z-LLL-AMC (C) and ubiquitin-AMC (D). In a separate treatment, PPi was added before measurement to spermatozoa preserved without PPi (Add PPi). As a negative control, 10 μM MG132 (a proteasomal inhibitor) was added to "No treat" and "PPi+BTS" spermatozoa on day 3. Experiments were repeated three times. Values are expressed as the mean of fluorescence intensity.
Figure 6B:
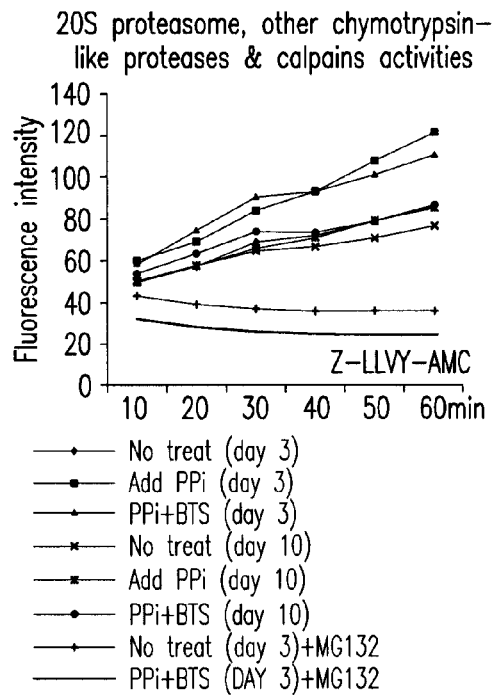
Figure 6C:
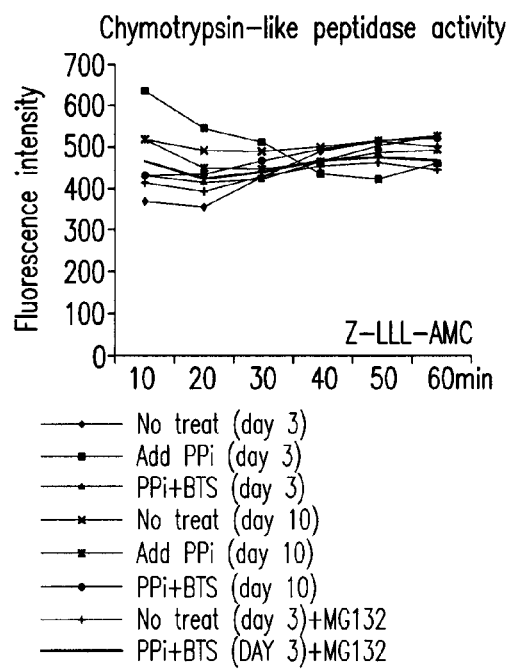
Figure 6D:
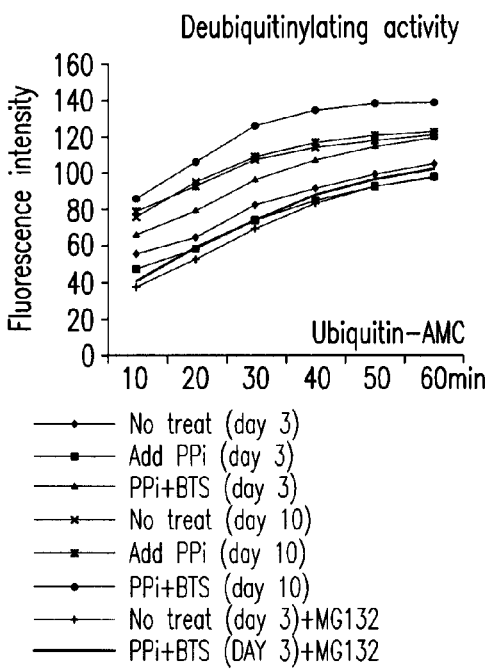

FIGS. 6A to 6D show the effects of PPi on proteasomal enzymatic activities of stored boar spermatozoa. As shown in FIG. 6A, higher chymotrypsin-like PGPH activity (Z-LLE-AMC substrate) was measured in Add PPi treatment on day 3 (relative fluorescence of 392.1; no units) and PPi+BTS on day 10 (relative fluorescence of 388), compared to other treatments (363.1-386.1; p<0.05). As shown in FIG. 6B, chymotrypsin-like proteasomal core activity (Z-LLVY-AMC substrate) gradually increased during measurement in all groups, and the PPi+BTS and Add PPi treatments showed higher fluorescence intensities with this substrate, compared to controls (110.8-121.5 vs. 85.7; p<0.05). The highest fluorescence intensity was observed in Add PPi at 10 min, but the intensity decreased progressively during measurement, and chymotrypsin-like activity showed no differences between treatments (FIG. 6C). On the contrary, a higher deubiquitinating activity (ubiquitin-AMC) was observed in PPi+BTS treatment on day 10, compared to other treatments (relative fluorescence of 138.9 vs. 98.4-122.7; FIG. 6D). As anticipated, low chymotrypsin-like activity was detected in spermatozoa treated with proteasomal inhibitor MG132. Overall, supplementation with PPi increased the proteasomal-proteolytic and deubiquitinating activities in spermatozoa and showed beneficial effects during sperm preservation.

Example 9

Figure 7:
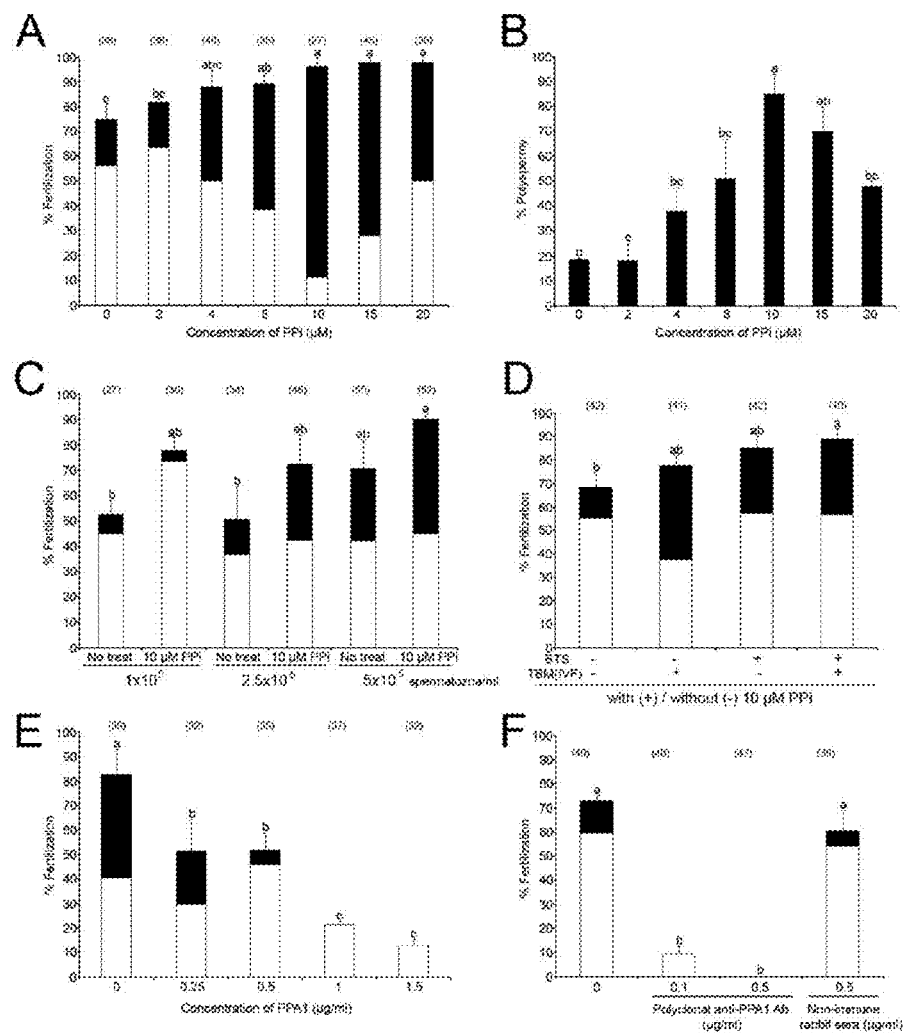
FIG. 7: Shows the effect of PPi on total and polyspermic fertilization during porcine IVF. Values are expressed as the mean percentages±SEM. □ % monospermic and ■ % polyspermic oocytes. Different superscripts a-c in each group of columns denote a significant difference at p<0.05. Numbers of inseminated ova are indicated in parentheses. (A) Porcine oocytes matured in vitro were inseminated with a standard concentration of $1\times10^6$ spermatozoa/ml, in the presence of ascending concentrations of PPi. Experiments were repeated five times. (B) The polyspermy rates, reflective of sperm fertilizing ability in vitro (same as panel A) dramatically increased in the presence of PPi. (C) Fertilization rates of porcine oocytes inseminated with different concentrations of spermatozoa in the presence/absence of 10 μM PPi. Experiments were repeated three times. (D) Fertilization rates of oocytes inseminated with boar spermatozoa preserved for 3 days in BTS with/without 10 μM PPi. Other porcine oocytes were inseminated (sperm conc. $5\times10^5$ spermatozoa/ml) with and without 10 μM PPi, with spermatozoa stored with and without PPi. Experiments were repeated three times. (E) Effect of extrinsic PPA1 enzyme on porcine IVF. Oocytes were inseminated with different concentrations of purified PPA1 protein. Experiments were repeated twice. (F) Porcine oocytes were inseminated in the presence of rabbit polyclonal anti-PPA1 antibody or non-immune rabbit serum (a control of PPA1 antibody). Experiments were repeated twice.
Figure 8:
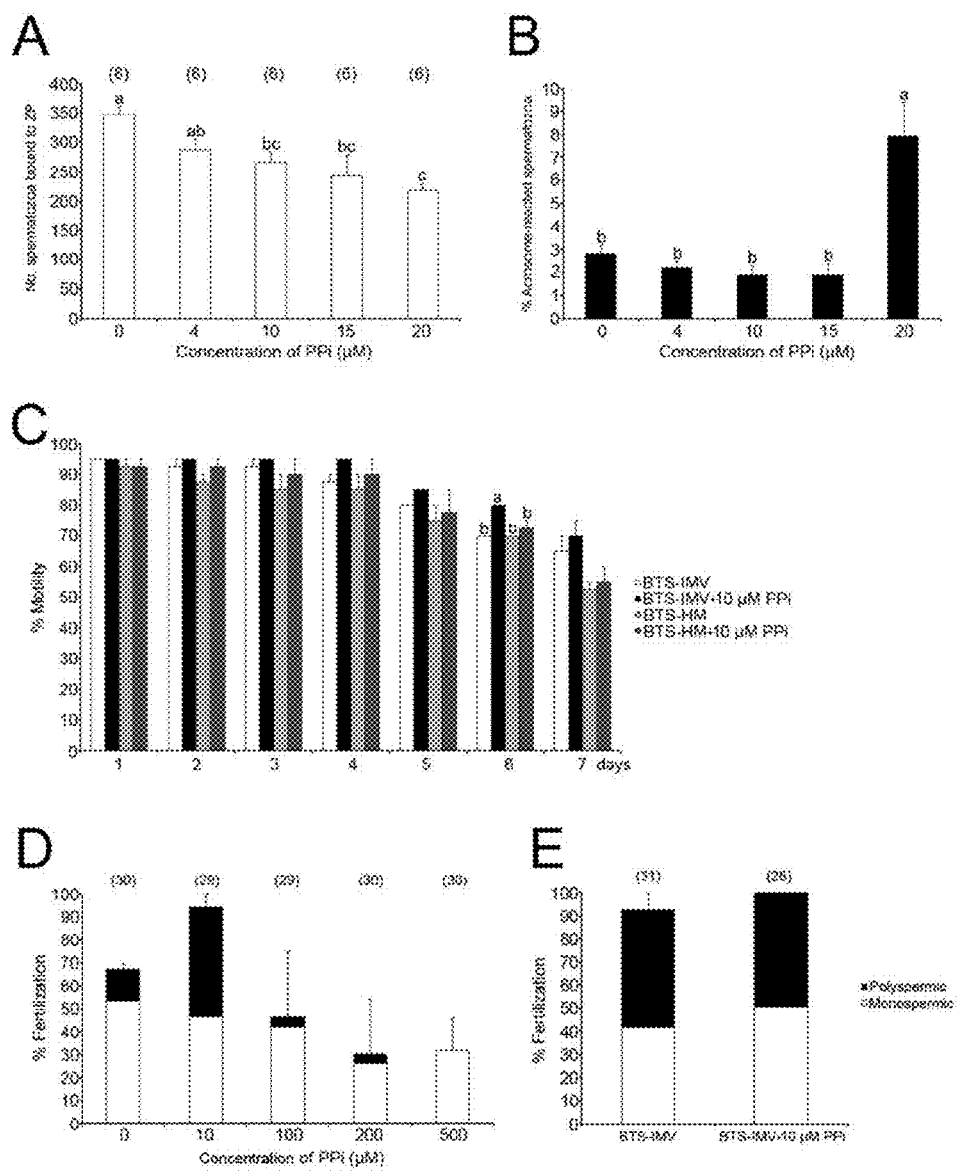
FIG. 8: (A) Shows the effect of PPi on sperm-zona binding. Porcine oocytes were inseminated (sperm conc. $5\times10^5$ spermatozoa/ml) with various concentrations of PPi for 30 min, fixed and stained with DNA stain DAPI. The numbers of spermatozoa bound per zona-pellucida (ZP) were counted under epifluorescence microscope. Values are expressed as the mean±SEM. Different superscripts a-c in each group of columns denote a significant difference at p<0.05. Numbers of inseminated ova are indicated in parentheses. (B) The percentage of acrosome-reacted spermatozoa of panel A (PNA-FITC stained). Values are expressed as the mean percentages±SEM. Different superscripts a & b in each group of columns denote a significant difference at p<0.05. (C) Effect of PPi supplementation on the viability of spermatozoa stored in commercial and custom made BTS extenders. Boar spermatozoa were preserved in BTS-IMV (IMV technologies, France) or BTS-HM (homemade) with and without 10 μM PPi for 7 days at room temperature. Sperm motilities were evaluated by observation under light microscopy at 37.5° C. Higher sperm motility was observed in BTS-IMV with PPi on day 6 than in any other group. Experiments were repeated twice. Different superscripts a, b in each group of columns denote a significant difference at p<0.05. (D) Excessive concentrations of PPi were added into IVF medium. Fertilization rates decreased with high concentrations of PPi. Experiments were repeated twice. Values are expressed as the mean percentages±SEM. □ % monospermic and ■ % polyspermic oocytes. Numbers of inseminated ova are indicated in parentheses. (E) Effect of PPi on fertilization with spermatozoa stored in commercial extender, BTS-IMV. Nearly 100% fertilization was achieved using spermatozoa preserved in BTS-IMV with 10 μM PPi (day 3). Experiments were repeated twice. Values are expressed as the mean percentages±SEM. □ % monospermic and ■ % polyspermic oocytes. Numbers of inseminated ova are indicated in parentheses.

PPi Enhances Sperm-Zona Penetration During Fertilization and Fertilizing Ability Following Extended Storage FIGS. 7A to 7F and FIGS. 8A to 8E illustrate the effects of PPi on total and polyspermic fertilization during porcine IVF (FIGS. 7A to 7F), and the effects of PPi on sperm-zona binding (FIGS. 8A to 8E). Porcine oocytes were fertilized in the presence of PPi at different concentrations (FIG. 7A). The rates of total and polyspermic fertilization increased significantly and progressively (up to 10 µM PPi) with increasing concentrations of PPi (p<0.05). The highest polyspermy was observed after addition of 10 µM PPi (84.9% polyspermy; FIG. 7B). The mean number of spermatozoa bound to ZP decreased slightly, but not significantly with increasing concentrations of PPi (FIG. 8A). However, the percentage of acrosome-reacted spermatozoa was significantly higher in the presence of 20 µM PPi than 0-15 µM PPi (p<0.05, FIG. 8B). Since a reduction of an insemination dose is desirable in AI settings, porcine oocytes were also inseminated with reduced sperm concentrations with and without 10 µM PPi. Consistently, the percentage of total and polyspermic fertilization was augmented by PPi at 1, 2, and 5×10⁵ spermatozoa/ml; the increase induced by PPi was statistically significant at 5×10⁵ spermatozoa/ml concentration (FIG. 7C). To determine if sperm storage in PPi-supplemented BTS extender has a beneficial effect on sperm fertilizing ability, freshly ejaculated boar spermatozoa were stored in BTS with or without 10 µM PPi for 3-4 days, and used for IVF in the presence or absence of 10 µM PPi. The fertilization rates were higher, and the polyspermy was highest of all treatments with addition of PPi during IVF, in the absence of PPi in TBM (FIG. 7D; second column). However, the highest combined (mono+polyspermic) fertilization rate was observed with spermatozoa preserved with 10 µM PPi in BTS when used for IVF without PPi addition (FIG. 7D; third column), or with PPi in IVF medium (FIG. 7D; fourth column). Altogether, PPi showed statistically significant (p<0.05), beneficial effects on sperm preservation and sperm fertilizing ability.

Control experiments were conducted to deplete sperm PPi with extrinsic inorganic pyrophosphatase in the form of purified PPA1. To incapacitate sperm-borne PPA1, porcine oocytes were fertilized in the presence of anti-PPA1 antibody. The specificity of both reagents was established by western blotting (see FIG. 3). Both PPA and anti-PPA1 antibody decreased the fertilization rate in a dose-dependent manner (FIGS. 7E & F). No significant differences in fertilization rates were observed when the anti-PPA1 antibody was replaced with normal serum during fertilization (FIG. 7F).

To assess possible variation between sperm storage media, boar sperm batches were preserved in commercial BTS (BTS-IMV, IMV Technologies, L'Aigle, France) or homemade BTS (BTS-HM) (Pursel et al., *J Anim Sci* 40:99-102, 1975) in the presence of 10 µM PPi for 7 days. Higher sperm motility was found in BTS-IMV+10 µM PPi on day 6 than in all other groups (FIG. 8C). Excess PPi added into IVF medium (100-500 µM PPi) decreased fertilization rates in a dose-dependent manner (FIG. 8D). In a separate trial, boar spermatozoa were stored in BTS-IMV with 10 µM PPi for 3 days, and used for IVF. Near 100% fertilization was observed with spermatozoa preserved with 10 µM PPi, compared to below 70% fertilization without PPi in BTS-IMV (FIG. 8E).

Example 10

Statistical Analysis

Analyses of variance (ANOVA) were carried out using the SAS package in a completely randomized design. Duncan's multiple range test was used to compare values of individual treatment when the F-value was significant (p<0.05).

While the invention has been described in connection with specific embodiments thereof, it will be understood that the inventive device is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth.

What is claimed is:

1. A sperm preservation media comprising inorganic pyrophosphate (PPi) and at least one spermatozoa, wherein the concentration of PPi is between about 1 µM and about 200 µM.

2. The sperm preservation media of claim 1, wherein the concentration of PPi is between about 1 μM and about 20 μM.

3. The sperm preservation media of claim 1, wherein the concentration of PPi is about 10 μM.

4. The sperm preservation media of claim 1, wherein said preservation media is used to preserve sperm from a porcine.

5. A media for sperm processing comprising inorganic pyrophosphate (PPi) and at least one spermatozoa, wherein the concentration of PPi is between about 1 μM and about 200 μM.

6. The media of claim 5, wherein the concentration of PPi is between about 1 μM and about 20 μM.

7. A media for in vitro fertilization (IVF) or artificial insemination (AI) comprising inorganic pyrophosphate (PPi) and at least one spermatozoa, wherein the concentration of PPi is between about 1 μM and about 200 μM.

8. The media of claim 7, wherein the concentration of PPi is between about 1 μM and about 20 μM.

9. A method of sperm preservation comprising storing sperm in a media comprising inorganic pyrophosphate (PPi), wherein the concentration of PPi is between about 1 μM to about 200 μM.

10. The method of claim 9, wherein the concentration of PPi is between about 1 μM to about 20 μM.

11. The method of claim 9, wherein the concentration of PPi is about 10 μM.

12. The method of claim 9, wherein the sperm is stored in the media comprising PPi for up to 10 days.

\* \* \* \* \*